United States Patent [19]

Griffin et al.

[11] Patent Number: 5,085,499
[45] Date of Patent: Feb. 4, 1992

[54] FIBER OPTICS SPECTROCHEMICAL EMISSION SENSORS

[75] Inventors: Jeffrey W. Griffin, Kennewick; Khris B. Olsen, West Richland, both of Wash.

[73] Assignee: Battelle Memorial Institute, Richland, Wash.

[21] Appl. No.: 239,778

[22] Filed: Sep. 2, 1988

[51] Int. Cl.$^5$ .................... G01N 21/67; G01N 21/68; G01N 21/69

[52] U.S. Cl. .................................. 356/311; 356/313; 356/316

[58] Field of Search ................ 356/311, 313, 314, 316

[56] References Cited

U.S. PATENT DOCUMENTS

| | | | |
|---|---|---|---|
| 3,909,133 | 9/1975 | Hobson et al. | 250/341 X |
| 3,909,652 | 9/1975 | Ferre et al. | 313/146 |
| 4,482,246 | 11/1984 | Meyer et al. | 356/316 |
| 4,509,212 | 4/1985 | Baker | 356/436 X |
| 4,516,858 | 5/1985 | Gelbwachs | 356/437 |
| 4,532,219 | 7/1985 | Hagen et al. | 356/316 X |
| 4,533,834 | 8/1985 | McCormack | 250/554 |
| 4,569,592 | 2/1986 | Osada et al. | 356/318 |
| 4,575,241 | 3/1986 | Demers et al. | 356/316 X |
| 4,586,368 | 5/1986 | Rice et al. | 73/23.1 |
| 4,616,137 | 8/1986 | Goff et al. | 250/554 |
| 4,644,173 | 2/1987 | Jeffers | 250/554 |
| 4,656,508 | 4/1987 | Yokota | 358/98 |
| 4,666,672 | 5/1987 | Miller et al. | 422/68 |
| 4,689,754 | 8/1987 | Collins et al. | 364/497 |
| 4,692,875 | 9/1987 | Riley et al. | 356/313 X |
| 4,711,572 | 12/1987 | Quillfeldt et al. | 356/316 X |
| 4,713,552 | 12/1987 | Denis et al. | 250/577 |
| 4,723,438 | 2/1988 | Adler-Golden et al. | 356/313 X |
| 4,732,477 | 3/1988 | Kumbrant | 356/313 |
| 4,766,318 | 8/1988 | Adler-Golden et al. | 356/313 X |
| 4,844,612 | 7/1989 | Durr et al. | 356/316 |

OTHER PUBLICATIONS

"A New He Discharge-Afterglow and Its Application as a Gas Chromatographic Detector", Spectrochimica Acia. vol. 40B, Nos. 10-12, pp. 1573-1584, 1985, Rice et al.

"Spectrochemical Analysis of Liquids Using the Laser Spark", Applied Spectroscopy, vol. 3B, No. 5, 1984, Cremers et al.

*Primary Examiner*—Vincent P. McGraw
*Attorney, Agent, or Firm*—Marger, Johnson, McCollom & Stolowitz, Inc.

[57] ABSTRACT

A method of in situ monitoring of a body of a fluid stored in a tank or groundwater or vadose zone gases in a well for the presence of selected chemical species uses a probe insertable into the well or tank via a cable and having electrical apparatus for exciting selected chemical species in the body of fluid. The probe can have a pair of electrodes for initiating a spark or a plasma cell for maintaining a plasma to excite the selected chemical species. The probe also has optical apparatus for receiving optical emissions emitted by the excited species and optically transmitting the emissions via the cable to an analysis location outside the well. The analysis includes detecting a selected wavelength in the emissions indicative of the presence of the selected chemical species. A plurality of probes can be suspended at an end of a respective cable, with the transmitting and analyzing steps for each probe being synchronized sequentially for one set of support equipment and instrumentation to monitor at multiple test points. The optical apparatus is arranged about the light guide axis so that the selected chemical species are excited the fluid in alignment with the light guide axis and optical emissions are received from the excited chemical species along such axis.

11 Claims, 14 Drawing Sheets

FIBER OPTICS SPECTROCHEMICAL EMISSION SENSORS

The United States Government has rights in this invention in accordance with the operating contract DEAC06-76RLO 1830 between Battelle Memorial Institute and the U.S. Department of Energy.

BACKGROUND OF THE INVENTION

This invention relates to remote monitoring of fluids for the presence of selected chemical species and, more particularly, to methods and apparatus for in situ monitoring of gases and liquids in ground water and in the vadose zone and liquid chemical waste storage tanks.

Many of the commercial and industrial activities throughout this country produce as by-products large quantities of a diverse variety of chemical wastes, including organic chemicals and radionuclides. It is known that many such chemicals are hazardous to persons and or the environment. It has therefore become increasingly important to test and monitor the environment, including ground water, gases, vadose zone and surface air to determine the presence of, and monitor concentrations of various chemical species. Such monitoring includes the need for monitoring substantial areas by testing at a plurality of thoughtfully positioned test points.

Spectrochemical emission methods have long been used in the laboratory for the detection of elemental and molecular chemical species. Various excitation mechanisms are used in conventional laboratory spectroscopy. These include flame excitation, spark excitation, arc excitation, and inductively coupled excitation. Inductively coupled excitation includes microwave-induced plasma (MIP) and radio-frequency inductively coupled plasma (ICP). For the most part, these analytical methods are embodied in laboratory instruments. Such instruments are physically large and expensive. Consequently, sample analysis is almost always performed in the laboratory.

Laboratory sample analysis is not well suited to environmental monitoring for several reasons. First, samples must be collected in the field and transported to the laboratory for analysis This is a costly and time-consuming procedure. Second, use of these discrete samples is inadequate for close observation of the dynamic ebb and flow of certain characteristics at a site, for example, in ground water. The inability to constantly monitor a site is exacerbated by the delays occasioned in processing discrete samples in overburdened laboratories having limited instrumentation.

Accurate monitoring of a large site requires testing at multiple test points. In doing so, the difficulties and expense of manual, discrete sampling techniques are multiplied. Additionally, it is extremely difficult and cumbersome to collect samples simultaneously from multiple test points by manual techniques.

A technique is known for in situ monitoring of molten metal. U.S. Pat. No. 4,732,477 shows a disposable probe for analyzing samples of molten charges inside the charges themselves. This apparatus is useful only for analysis of a single sample, and cannot be used thereafter, because use of the probe requires solidifying a sample of the molten charge inside a cavity in the probe. The patent shows the use of a light-transmitting body positioned with one end in the cavity of the mold and having a connection to a fiber-optical light conductor extending upwardly through a sample rod to a treating unit such as a spectrometer.

U.S. Pat. No. 4,692,875 shows a metal-alloy indentifier system in which a grinding wheel is used to produce sparks of glowing hot metal Light emitted by the sparks is transmitted via optical cable to a spectrometer for analysis and comparison of the "full spectrum signature" of the metal alloy with similar plots for alloys of known composition, to establish the unknown composition by a positive match with a known alloy.

U.S. Pat. No. 4,666,672 discloses an "optrode" for sensing halogenated hydrocarbons. The apparatus shown in that patent utilizes fluorometric detection of polyhalogenated hydrocarbons. The foregoing patents do not adequately address the problems outlined above.

Accordingly, a need remains for a way to monitor gases and liquids for selected chemical species in situ, in groundwater, the vadose zone and storage tanks.

SUMMARY OF THE INVENTION

It is an object of the present invention to provide a faster alternative to present procedures for monitoring sites for the presence or concentration of selected chemical species. Another object is to reduce the cost of such monitoring.

A further object of the present invention is to allow simultaneous monitoring at a plurality of test points within the same locale. Still a further object of the present invention is to provide methods and apparatus for continuous monitoring for the presence of selected chemical species.

Yet another object of the invention is to enable in situ monitoring for the presence of selected chemical species, thereby obviating the delay and expense of present discrete grab sampling techniques. Yet a further object is to provide for in situ monitoring of fluids, including vapors and aerosols The present invention includes a method of in situ monitoring of a body of a fluid, for example, in a tank or well, for the presence of selected chemical species. The method includes providing a probe having electrical apparatus for exciting a sample of the fluid. For example, the probe may have a pair of electrodes for initiating a spark or it may have a plasma cell for maintaining a plasma to excite the selected chemical species. The probe also has optical apparatus for receiving optical emissions emitted by the excited sample and transmitting the emissions to a monitor. The method includes inserting the probe on an end of a cable into the well to place the probe in contact with the fluid. The next step is electrically transmitting an electrical signal via the cable to the probe for exciting the selected chemical species in situ in the fluid. The optical emissions from the excited chemical species are received in the probe. A portion of these emissions are optically transmitted via the cable to an analysis location outside the well. The final step is analyzing the emissions at the analysis location for indications of the presence of the selected chemical species. The analysis includes detecting a selected wavelength in the emissions indicative of the presence of the selected chemical species.

The foregoing method can include providing a plurality of probes, each suspended at an end of a respective cable; transmitting the signal to each of the probes via its respective cable; analyzing each probes's optical emissions; and further include synchronizing the transmitting and analyzing steps for each probe. This synchronous transmitting and analyzing may be done sequentially with respect to each of the probes so that one set of support equipment and instrumentation is used to operate a plurality of probes to monitor at multiple test points. Another aspect of the invention includes repeating the transmitting and analyzing steps, periodically or randomly, for a predetermined period of time to monitor the body of fluid essentially continuously during said period of time. This is the antithesis of manual, discrete sampling.

According to another feature of the invention, the optical apparatus includes an elongate light guide defining an axis, exciting the selected chemical species includes exciting the fluid in alignment with the light guide axis, and receiving optical emissions includes receiving emissions from the excited chemical species along said axis.

One embodiment of the invention includes exciting the selected chemical species by directing the electrical signal to initiate a spark in the presence of the fluid. Additionally, the electrical signal can be repetitive for repeatedly initiating a spark and the analyzing include integrating, during each of a series of time intervals each of a predetermined duration $t_1$, a detector signal responsive to the selected emission wavelength, synchronizing the integrating time intervals to the spark initiation so that each integrating interval begins approximately when a spark is initiated. In doing so, the electrical signal repeats such that the time between every repetition of the electrical signal and the next subsequent repetition is greater than $t_1$.

In an alternate embodiment of the invention, the selected chemical species is excited by maintaining a plasma in a cell in the probe and subjecting the fluid to the plasma. There, the electrical signal may be an RF signal coupled to the cell for exciting a gas to maintain the plasma. Helium is preferred, though any gas capable of maintaining a plasma may be used. Other examples include air, argon and nitrogen.

The present invention further includes a probe for in situ monitoring of a fluid analyte for the arrangement of the presence of selected chemical species. The probe comprises an elongated probe body of a predetermined diameter having first and second ends, an elongate light guide having first and second ends and defining an axis through said ends, a terminal portion of the light guide adjacent the first end extending axially into the first end of the probe body, an electrical conductor having first and second ends connected at the first end to the probe for providing an electric signal to the probe, means disposed in the second end of the probe body for admitting the fluid analyte axially of the first end of the light guide, excitation means coupled to the first end of the conductor and responsive to the electric signal for exciting components of the fluid analyte along a portion of the light guide axis in proximity to the first end of the light guide, the light guide first end including means adapted to receive optical emissions from the excited components of the fluid analyte for transmitting the optical emissions to a detector coupled to the second end of the light guide.

In such a probe, the excitation means may include a pair of spaced apart electrodes defining a spark gap between the electrodes for generating a spark. The probe may further include trigger means for generating a trigger signal responsive to the spark and trigger signal means for transmitting the trigger signal to the detector. More specifically, the electrodes may be formed of thoriated tungsten and the light guide may be a fiber optic cable with the first end positioned adjacent the spark gap.

In a preferred embodiment of the invention, the probe body is formed of a substantially rigid, waterproof non-conductive material and includes a first bore extending into the probe body from the first end alongside the fiber optic cable, sized to receive a first wire. The probe body further includes a second bore extending into the probe body from the first end alongside the fiber optic cable, sized to receive a second wire. Further, the body includes an analyte cavity extending into the probe body from the second end to the first end of the fiber optic cable. In such an arrangement, the conductor includes the first and second wires, the analyte admitting means includes the analyte cavity, and the electrodes are positioned in the probe body so that one of the electrodes contacts the first wire and the other electrode contacts the second wire and each of the electrodes extends into the analyte cavity adjacent the first end of the fiber optic cable.

An alternate embodiment of the invention includes the probe just described, wherein the excitation means includes an elongate capillary tube aligned about the light guide axis, the tube having first and second ends and having input and discharge ports; the first end of the capillary tube positioned in optical communication with the first end of the light guide; the second end of the capillary tube connected to the analyte admitting means to receive analyte into the capillary tube; a first tube connected to the input port for supplying inert gas; a second tube connected to the discharge port for providing a vacuum source; an electrode capacitively coupled to the capillary tube and connected to the conductor to receive the electric signal for exciting the inert gas; and a ground electrode coupled to the tube for grounding current flow in the gas.

In one operative example of the probe, the electrode is a cylinder formed of stainless steel and is positioned concentrically about the capillary tube; the capillary tube is formed of quartz; the light guide includes a fused silica fiber optic cable; and the probe further comprises a gradient index lens positioned between the first end of the capillary tube and the first end of the fiber optic cable for focusing optical emissions from the tube into the fiber optic cable.

The present invention further includes a system for in situ monitoring of a fluid analyte for the presence of selected chemical species. The system comprises a probe such as described above; an elongate cable having first and second ends and comprising the electrical conductor and the light guide, connected at the first end to the probe, for positioning the probe in contact with the fluid analyte; power supply means connected to the second end of the conductor for providing the electrical signal to the excitation means; and detector means connected to the second end of the light guide for detecting the presence of selected wavelengths of light indicative of the presence of the selected chemical species. When the alternate embodiment of the probe is used, the excitation means includes a plasma cell and the cable further includes a gas line for transmitting gas along the cable to operate the probe.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 10 is a spectral plot of air generated by the spark probe apparatus of FIG. 6. It comprises three sheets:

DETAILED DESCRIPTION OF A PREFERRED EMBODIMENT

Figure 1:
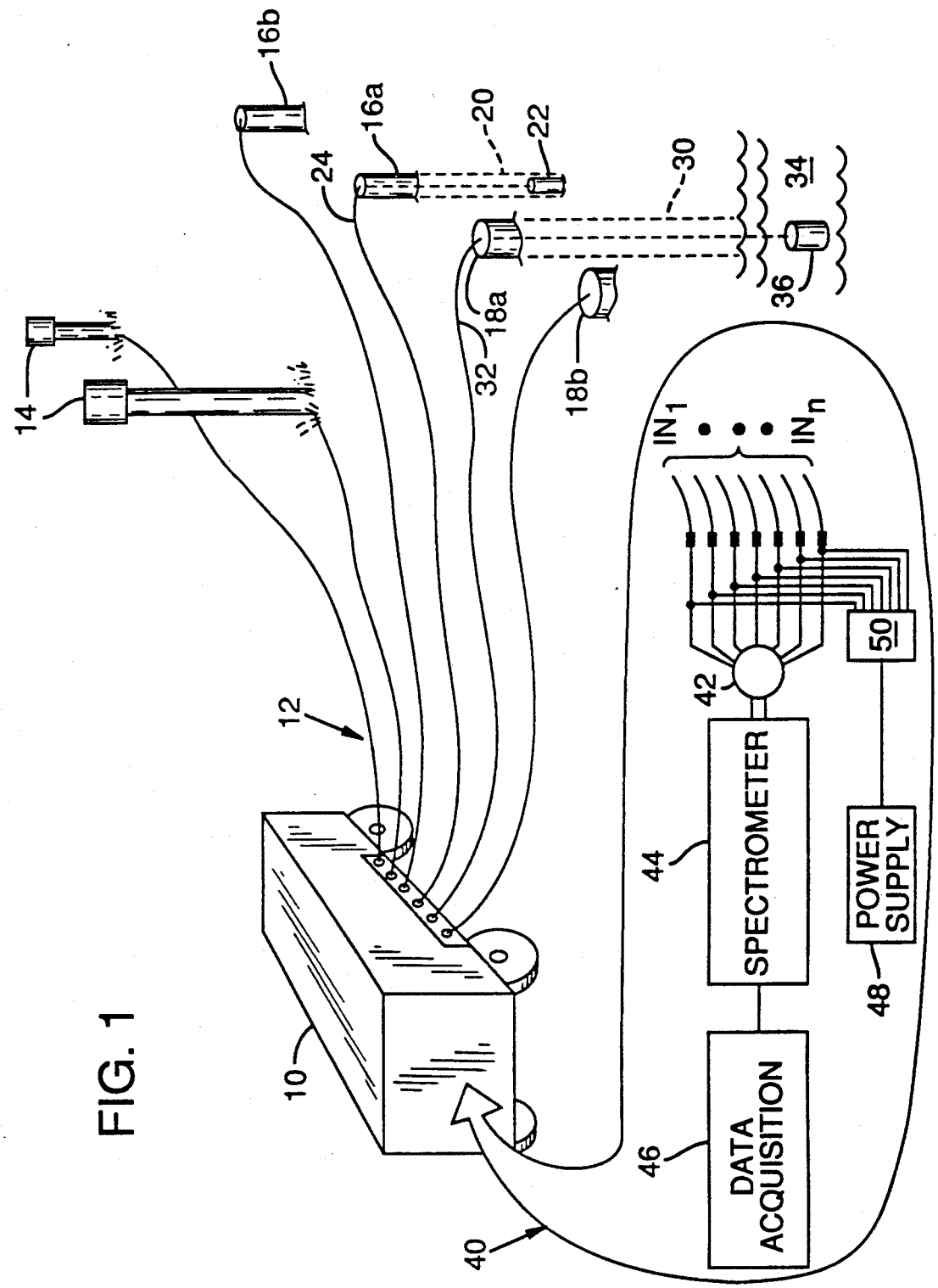
FIG. 1 is a conceptual diagram of an in-situ chemical monitoring system according to the present invention including an instrumentation trailer containing equipment for operating several probes and instrumentation for analyzing data from the probes and showing multiple probes connected via cables to the trailer for simultaneous monitoring of groundwater, vadose zone and atmospheric sites.

FIG. 1 depicts a multi-probe system for monitoring groundwater, vadose zone and atmospheric test locations for the presence and/or to measure concentrations of one or more selected chemical species. The system includes an instrumentation trailer 10 which contains various equipment as will be further described herein. Several cables 12 are provided, each cable interconnecting the instrumentation trailer 10 to a probe. Each cable contains an optical fiber, a power cable, gas supply, or the like.

For monitoring ground water, a well or shaft 18A, 18B is provided, extending from the surface down to the ground water. The portion of well 18A that extends below the surface is shown by dashed lines 30. It extends down into ground water 34. A ground water probe 36 is suspended down through well 18A into the water 34 by cable 32. Cable 32 is connected at the other end to the instrumentation trailer 10.

For monitoring the vadose zone, shafts are provided which need not extend as far as the ground water. For example, shaft 16A is provided for this purpose. The subsurface portion of shaft 16A, shown by dashed line 20, extends below the surface but not into ground water. A vadose zone probe 22 is deployed in shaft 16A, suspended in the vadose zone by cable 24. Again, the other end of the cable is connected to the instrumentation trailer 10.

For atmospheric monitoring, one or more additional probes such as probe 14, may be positioned atop a pole at a desired height. Atmospheric probes also are connected to the instrumentation trailer via a cable.

Equipment 40 is housed in the instrumentation trailer 10 for operating the probes and acquiring, storing and analyzing data from the probes. Preferably, the trailer 10 is mobile and self-contained for operation at any desired location. Equipment 40 includes an optical switch 42. Each of the cables 12, connected to a probe at one end, includes a light guide which is connected to one of the inputs $IN_2$ through $IN_N$ to the optical switch 42. Optical switch 42 provides for selecting the optical emissions from one of the light guides at a time for analysis. A spectrometer and detection system 44, more fully described below, is connected to receive the optical emissions selected by optical switch 42. Data acquisition and analysis instrumentation 46 is connected to receive information provided by the spectrometer and detection system 44.

Operation of the probes requires that they receive certain electrical signals, as more fully described in subsequent sections. Such electrical signals may be provided by a power supply 48. Power supply 48 provides the signals to a switch 50 which may be any suitable solid-state or electro-mechanical switching device for directing the electrical signals to a selected one of the probes at a time. Accordingly, each probe cable 12 includes at least one electrical conductor for receiving an electrical signal from the power supply switch 50.

In subsequent sections, two different types of probes are disclosed for use in an in situ chemical monitoring system such as that depicted in FIG. 1. The equipment required for operating and appropriate instrumentation for receiving and processing information received from each type of probe will be described. The first type of probe is an RF induced plasma probe, described in the next section. Subsequently, a spark excitation probe is disclosed. Any combination of either or both types of probes may be incorporated in a system such as that shown in FIG. 1. The plasma probe is suitable for use in vapors or aerosols. The spark probe may be used in essentially any fluid, including liquids. The term "fluid" as used herein shall include liquids and vapors. Substantial savings may be realized in a system of that type because the equipment for operating the probes and the instrumentation for receiving and processing information from the probes is shared among all of the probes by use of the optical switch 42 and electrical switch 50 as described above. This equipment and instrumentation is described in the following sections with respect to a single probe for purposes of illustration.

RF Induced Plasma Excitation

Plasma excitation is a laboratory analysis technique that employs a radio frequency-induced plasma for analyte excitation. This technique is known for use in laboratory sensors for vapor analysis, especially from gas chromatographic columns. Generally, in this technique, a plasma is sustained while a small amount of analyte gas is introduced into the plasma volume. The plasma atoms, for example, helium, are efficient excitors of a number of chemical species. Consequently, observation of spectral emissions from the plasma at a wavelength other than that for the plasma reveals spectral emission lines due to the analyte species.

There are two popular configurations of the plasma excitation scheme. In the first, the gas is flowed through a microwave cavity operating typically at 2.45 GHz. This configuration is referred to as the MIP or microwave-induced plasma. The stringent design requirements on microwave power transmission systems and cavities virtually eliminates this method from consideration for in situ use.

A second configuration excites the plasma working gas at a much lower frequency, typically 20 to 300 KHz. Helium excitation at 26-27 KHz is used in a laboratory apparatus described by Rice, D'Silva and Fassel; "A new He discharge-afterglow and its application as a gas chromatographic detector", *Spectrochimica Acta*, Volume 40B, Nos. 10-12, pp. 1573-84, 1985.

Figure 2:
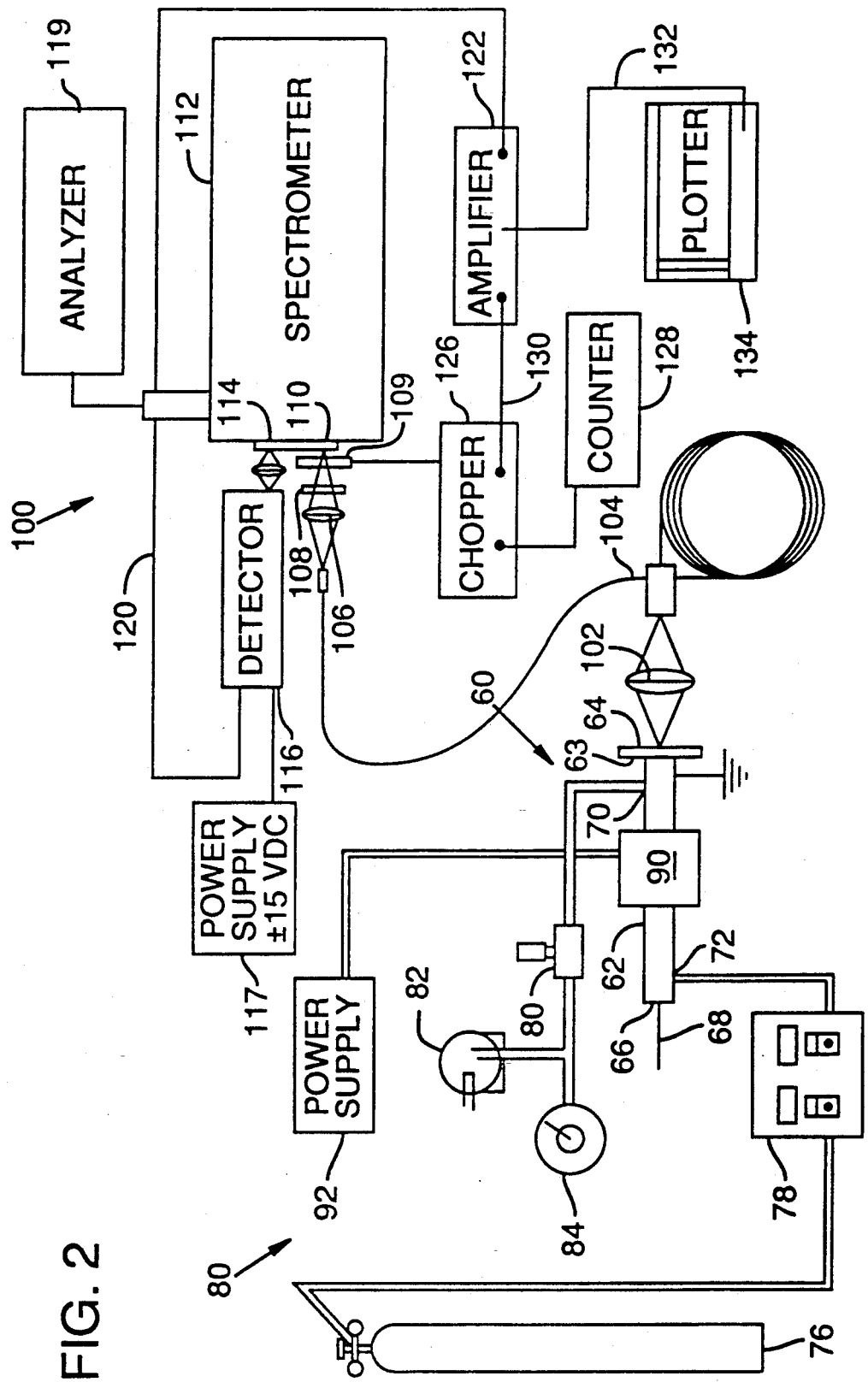
FIG. 2 is a schematic diagram of an example of an RF induced plasma apparatus, support equipment connected for operating the plasma apparatus and instrumentation connected for receiving, storing and analyzing data acquired from the plasma apparatus.

FIG. 2 is a schematic diagram of a radio frequency plasma apparatus 60, operating equipment 80 connected for operating plasma apparatus 60, and instrumentation 100 connected for receiving and analyzing information received from plasma apparatus 60.

Plasma apparatus 60 includes a hollow elongate vessel 62 for containing the plasma. The vessel 62 may be referred to as the plasma cell. The plasma cell includes an open first end 63. A window 64 is connected over the first end 63. The window 64 is made of a material that is transparent to wavelengths of interest. Thus, spectral emissions along the cell axis are emitted through window 64. Axial viewing of the plasma cell emissions has been found to yield superior results as compared to transverse viewing, i.e. across the capillary tube. The axial viewing presents a longer optical depth. Additionally, some degree of collimation of the optical emissions occurs due to Fresnel reflection of the plasma/glass interface.

The cell 62 has an aperture 66 in the second axial end. A capillary tube 68 extends into cell 62 through aperture 66. In the preferred embodiment, capillary tube has an inlet with a diameter of about 10 μm. Capillary tube 68 allows a small amount of analyte to enter cell 62 for excitation by the plasma. The specific geometry of an operative example of a plasma cell is described subsequently.

The equipment for sustaining the plasma is next described. The cell 62 includes an inlet port 72 and a discharge port 70. Inlet port 72 is connected to a source of relatively pure (99.99%) gas, for example, helium. Preferably, a helium source 76 is connected to a mass flow controller 78 for dispensing the helium to inlet port 72 at a controlled flow rate. In the preferred embodiment, the flow controller 78 is a Matheson Dyna Blender model SP-760. Discharge port 70 is connected through a metering valve 80 to a vacuum pump 82. A gauge 84 may be provided for monitoring and setting the desired pressure. In the preferred embodiment, the metering valve 80 is a Whitney Micro-metering valve model SS-22RSH, the vacuum pump 82 is a Gast model 0211-103A-G8C, and the gauge 84 is a Wallace and Tiernan 0-800 Torr gauge. The gas provided to the inlet port 72 may be any gas capable of sustaining a plasma. Examples include air, argon and nitrogen. Helium is preferred as it is an efficient exciter of various other species.

In operation, vacuum pump 82 maintains sub-atmospheric pressure in cell 62. Accordingly, analyte is drawn into cell 62 through capillary tube 68. Analyte gas and helium are constantly withdrawn from the cell through discharge port 70. Thus, the apparatus described allows continuous monitoring of fresh samples of analyte. Such continuous monitoring is in contradistinction to known methods of collecting and testing discrete samples of analyte.

Helium in cell 62 is excited by the application of radio frequency electrical signals. The electrical signals are capacitively coupled to cell 62 by an electrode 90. The electrode 90 is connected to a power supply 92, desirably an ENI model HPG-2 for providing radio frequency signals at predetermined voltages and frequencies. In the preferred embodiment, the plasma apparatus 60 is implemented in a probe for use as described above with reference to FIG. 1. Accordingly, the cable for interconnecting such a probe to the instrumentation trailer 10 would include a tube connected to input port 72 for helium supply, a second tube connected to the output port 70 for connecting to the vacuum source, and at least one electrical conductor connected to the electrode 90 for providing the electrical signal. Additionally, a fiber optic cable is employed as further described below.

Nominal operating parameters for maintaining a suitable helium plasma in cell 62 are shown in the following table:

TABLE I

Nominal Plasma Operating Parameters
1. Pressure: 200 TORR
2. He Flow Rate: 50 ml/min
3. Air Flow Rate (10 micron capillary): 45 ul/min
4. Excitation Frequency: 278 KHz
5. Excitation Voltage: 9.1 KV p-p
6. Power: 52 W (load), 20 W (forward)

Transmitting and Analyzing Optical Emissions

Apparatus for receiving and analyzing the optical emissions of plasma cell 62 are described next. Referring again to FIG. 2, a lens 102 may be provided for focusing light emitted through window 64 from plasma cell 62. A fiber optic cable 104 is positioned to receive the optical emissions. It is axially aligned with plasma cell 62 and the end of cable 104 positioned adjacent window 64 to optically coupling the plasma cell to the fiber optic cable. In the preferred example, cable 104 is a 12 meter length of Superguide fused silica fiber having a 1000 $\mu$m core with a loss of 17 db/km @0.6 $\mu$m.

The other end of fiber optic cable 104 is connected to direct the optical emissions through a lens 106, a filter 108, a chopper housing 109 and into the entrance slit 110 of a spectrometer 112. The spectrometer 112 is desirably a Jarrel Ash 1M Czerny Turner scanning spectrometer, with a model 1453 head. The spectrometer 112 is also coupled to an optical switching multi-channel analyzer 119, desirably an EG&G model PAR 1450. The spectrometer emits a selected wavelength portion of the emissions out of an exit slit 114. Alternatively, the spectrometer can be set to sweep over a range of wavelengths for producing a spectral plot of the optical emissions. Light emitted through exit slit 114 is directed to a detector 116 for converting the light into an electrical signal. Detector 116 is desirably an EG&G silicon detector model SDG040B. The electrical signal generated by detector 116 is connected over a path 120 to the signal input of a lock-in amplifier 122, desirably an Ithaco model 397EO. Power for detector 116 is supplied by power supply 117, desirably a Power Design model TW5005.

A sync connection 130 connects a chopper 126 to the sync input of the lock-in amplifier. Chopper 126 controls the chopper shutter 109 and is desirably a Laser Precision model CTX-534. A counter 128 may be connected to the chopper to precisely control [or monitor] the chopper frequency and is desirably a Data Precision model 5740. The chopper and lock-in amplifier are arranged to reject ambient light, as is known in the field, so their operation is not further described.

Operating parameters for an operative example of an electro-optical detection system as described above are shown in the following table:

TABLE II

Electro-Optical Detection System Parameters
He-Plasma Probe
1. Chopper: 140 Hz
2. Blocking Filter: Oriel RG780
3. Slit Width: 500 micron
4. Scan Rate: 3 Angm/sec
5. Lock-In Sensitivity: 10–100 mV
6. Lock-In Time Constant: 0.08 sec Lock-in amplifier 122 provides a filtered output signal over path 132. This output signal may be input to a storage device for subsequent retrieval and/or further processing. For example, the output signal may be converted to digital data by known methods and input to a digital computer system. Path 132 is shown in FIG. 2 connected to a plotter, such as an HP model 7046, 134 for generating a spectral plot when the spectrometer is operated in scanning mode.

Figure 3:
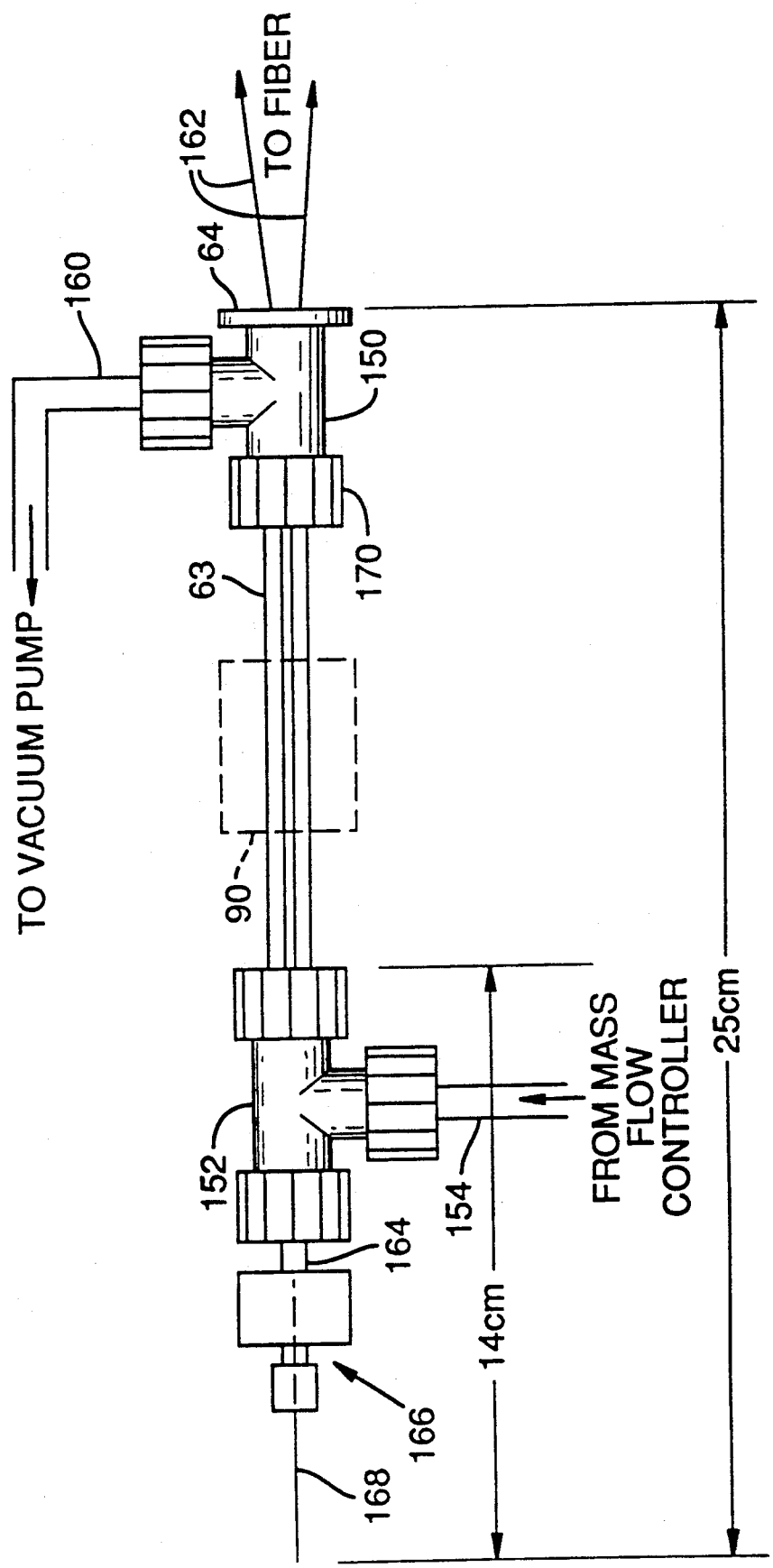
FIG. 3 is a side elevational view showing in detail the plasma cell of the apparatus shown in FIG. 2.

FIG. 3 is a side elevational view showing in greater detail one example of a plasma cell suitable for use as in FIG. 2. In this example, the plasma cell (62 in FIG. 2) is implemented as a quartz (fused silica) capillary tube 63. Capillary tube 63 has a 1.5 mm bore and 6 mm outside diameter. Tee fittings 150 and 152 are connected to first and second ends, respectively, of the capillary tube 63, and are sealed with O-ring seals. About 8 cm of capillary tube 63 is exposed between the two tee fittings.

Each tee fitting has first and second axially aligned apertures and a central aperture directed perpendicular to the axis of the aligned apertures. Thus, a first aligned aperture of tee 150 is connected covering the first end of capillary tube 63. The second aligned aperture of tee 150 is covered by a window 64. Window 64 is formed of a flat disc of fused silica 25 mm in diameter and 2.4 mm thick. The central aperture of tee 150 provides a discharge port. It is connectable to a tube 160 for providing a vacuum source to withdraw gases from capillary tube 63. In this arrangement, optical emissions generated within capillary tube 63 pass through window 64 generally defining a path indicated by arrows 162.

The second end of capillary tube 63 is connected to one of the axially aligned ports of tee fitting 152. The central aperture of tee 152 provides an inlet port. It is connectable to a tube 154 for receiving a supply of helium or other gas into the capillary tube. The other aligned port of tee 152 is connected, through a connecting tube 164, to a reduction union 166. Finally, a fused silica capillary tube 168 is connected and sealed to the reduction union, axially aligned with capillary tube 63. Capillary tube 168 is approximately 38 mm long, 2.5 mm in external diameter, and has a 10 micron bore. It admits analyte gas into capillary tube 63 for testing. Alternatively, a semi-permeable membrane may be used instead of the fused silica tube to admit analyte into capillary tube 63. One example of such a membrane is Teflon ®.

A cylindrical stainless steel electrode 90 (shown in phantom) is positioned coaxially about an exposed portion of capillary tube 63 for providing the RF excitation signal. The electrode 90 is electrically connected to a power supply (not shown). In this example, electrode 90 is formed of stainless steel approximately ⅛" thick. It may be mounted, for example, in a Teflon ® form for positioning relative to the capillary tube. Tee 150 serves as a ground electrode. It is grounded via connection 170. Accordingly, when a plasma is sustained in the capillary tube, current in the gas tends to flow generally in a direction from electrode 90 toward tee 150. In the preferred embodiment, plasma cell 62 has an operating pressure of 200 Torr, a helium flow rate of 50 ml/min, an air flow rate of 45 $\mu$l/min, and consumes 52 watts of power.

Figure 4A:
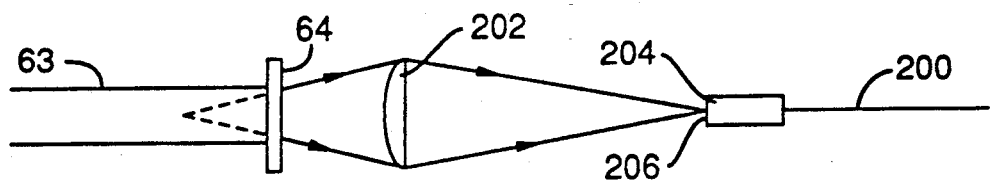
FIG. 4A is a schematic diagram of a portion of FIG. 2 showing in detail the optical elements arranged for collecting optical emissions from the plasma cell and inputting them into the fiber optic cable for transmission to the spectrometer.

FIG. 4A shows an operative example of interfacing the first end of capillary tube 63 to a fiber optic cable 200. The first end of capillary tube 63 is shown with the window 64 covering the end of the tube. A lens 202 is positioned spaced apart from window 64 and coaxially aligned to receive optical emissions that pass through window 64 from capillary tube 63. In this example, lens 202 is spaced 44 mm apart from window 64. Lens 202 is 25 mm in diameter and has a focal length of 25 mm. Fiber optic cable 200 terminates in an aluminum ferrule 204. Ferrule 204 ideally potted, polished, and fabricated of aluminum, is positioned axially aligned with capillary tube 63 and spaced approximately 83 mm from the incident surface of lens 202 so that optical emissions originating in the tube 63 are focused on the end 206 of ferrule 202. This arrangement provides an efficient interface between the plasma cell and the fiber optic cable.

Figure 4B:
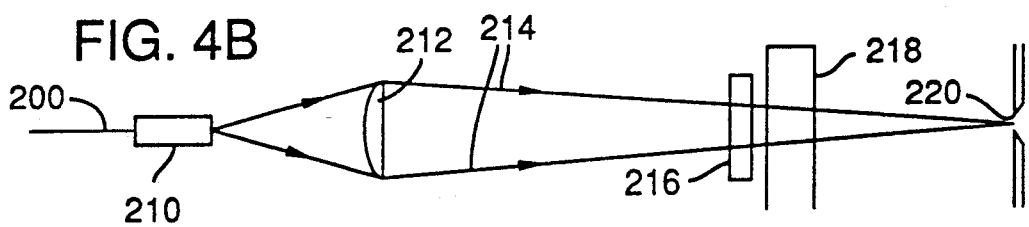
FIG. 4B is a schematic diagram of a portion of FIG. 2 showing in detail the optical elements arranged for receiving the optical emissions from the fiber optic cable and inputting them into the entrance slit of the spectrometer.

FIG. 4B shows an operative example of apparatus for receiving the optical emissions at the other end of fiber optic cable 200. This second end of cable 200 terminates in a ferrule 210. A lens 212 is spaced about 67 mm apart from ferrule 210, aligned to collect light emitted from the cable 200. Light that passes through lens 212 is indicated by lines 214. A long-pass filter 216 is disposed to filter the collected light 214. Filter 216 is designed, for example, to pass light having a wavelength greater than 780 nm. The lens 212 is spaced about 165 mm from entrance slit 220 of a spectrometer. The entrance slit 22 is about 300 μm. A chopper housing 218 is positioned between filter 216 and entrance slit 220 for interrupting the light beam, as described above. Lens 212, filter 216, chopper housing 218 and entrance slit 220 correspond to elements 106, 108, 109 and 110, in FIG. 2, respectively.

RF Induced Plasma Probe

Figure 5:
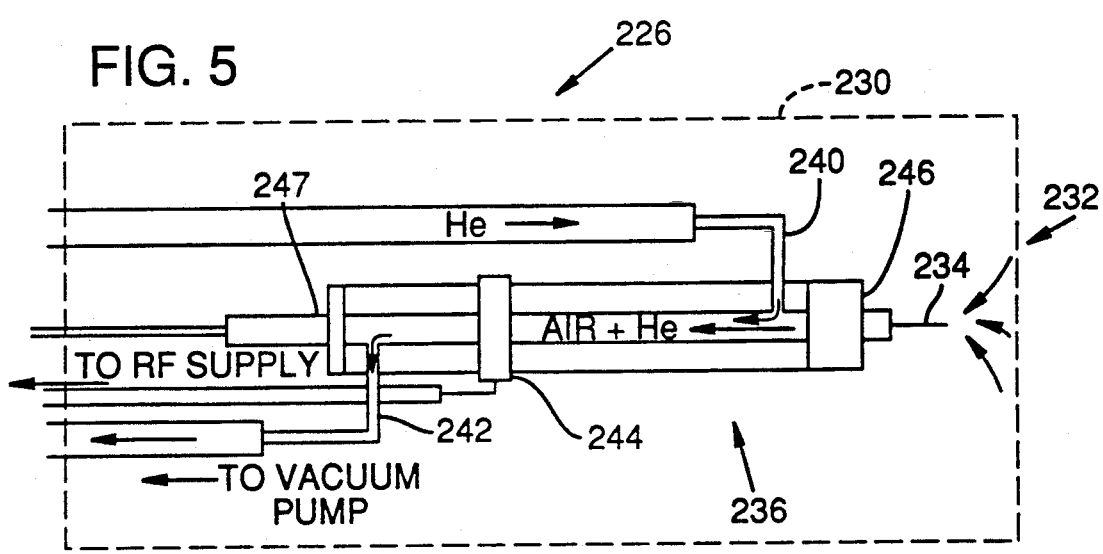
FIG. 5 is a schematic diagram in side view of an RF induced plasma probe suitable for use in the system of FIG. 1 in conjunction with support equipment and instrumentation such as shown in FIG. 2.

FIG. 5 shows the general arrangement of a plasma excitation probe 226. An elongate housing, indicated by dashed line 230, is provided for protecting the probe's internal components and shielding them from the elements. Housing 230 is formed of a sturdy, waterproof, non-conductive material. One end 232 of housing 230 is adapted to admit ambient air into the probe. End 232 may include a coarse screen, semi-permeable membrane, or both, so as to provide mechanical protection while allowing ambient air to enter the apparatus for chemical monitoring.

A silica capillary tube 236 is mounted axially in housing 230. An inlet port 240 and a discharge port 242 are formed extending radially in the capillary tube for receiving and discharging gas, respectively. These ports obviate the tee fittings employed in the laboratory apparatus. An excitation RF electrode 244 is substantially as described above. A cylindrical ground electrode 246 is connected over the analyte receiving end of tube 236. A capillary tube or critical orifice 234 is coupled to the analyte receiving end of tube 236. Ground electrode 246 may be connected by a wire, not shown, back to the power supply on the surface. Alternatively, a local earth ground could be employed, for example, by providing a conductor that extends outside probe 226 for contacting an interior wall of a test well. A gradient index lens 247 is connected to the end of capillary tube 236 opposite the intake end to focus the emitted light into the fiber optic cable.

Figure 12:
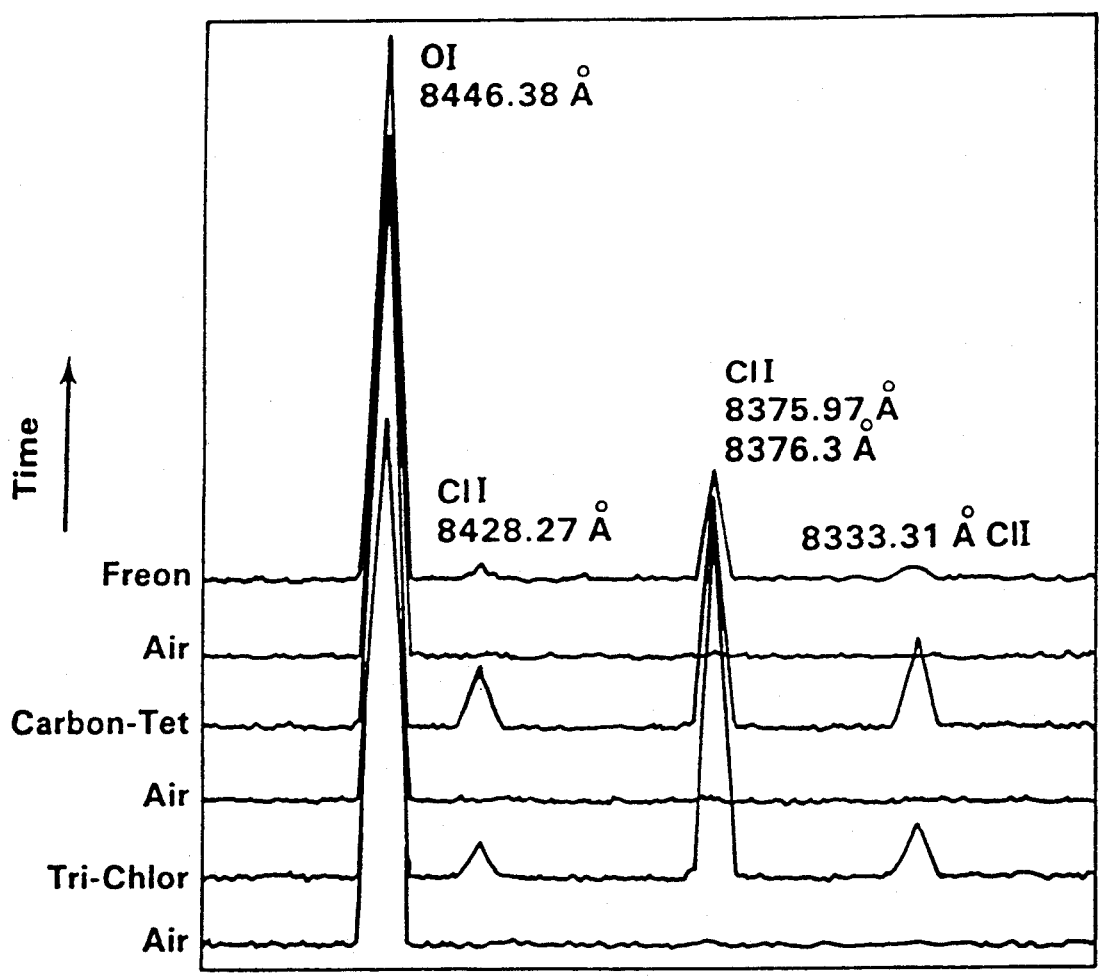
FIG. 12 shows the spectra obtained with the helium plasma probe in the presence of chlorinated hydrocarbons in air.

FIG. 12 shows the spectra obtained with the helium plasma probe in the presence of chlorinated hydrocarbons in air.

Figure 13:
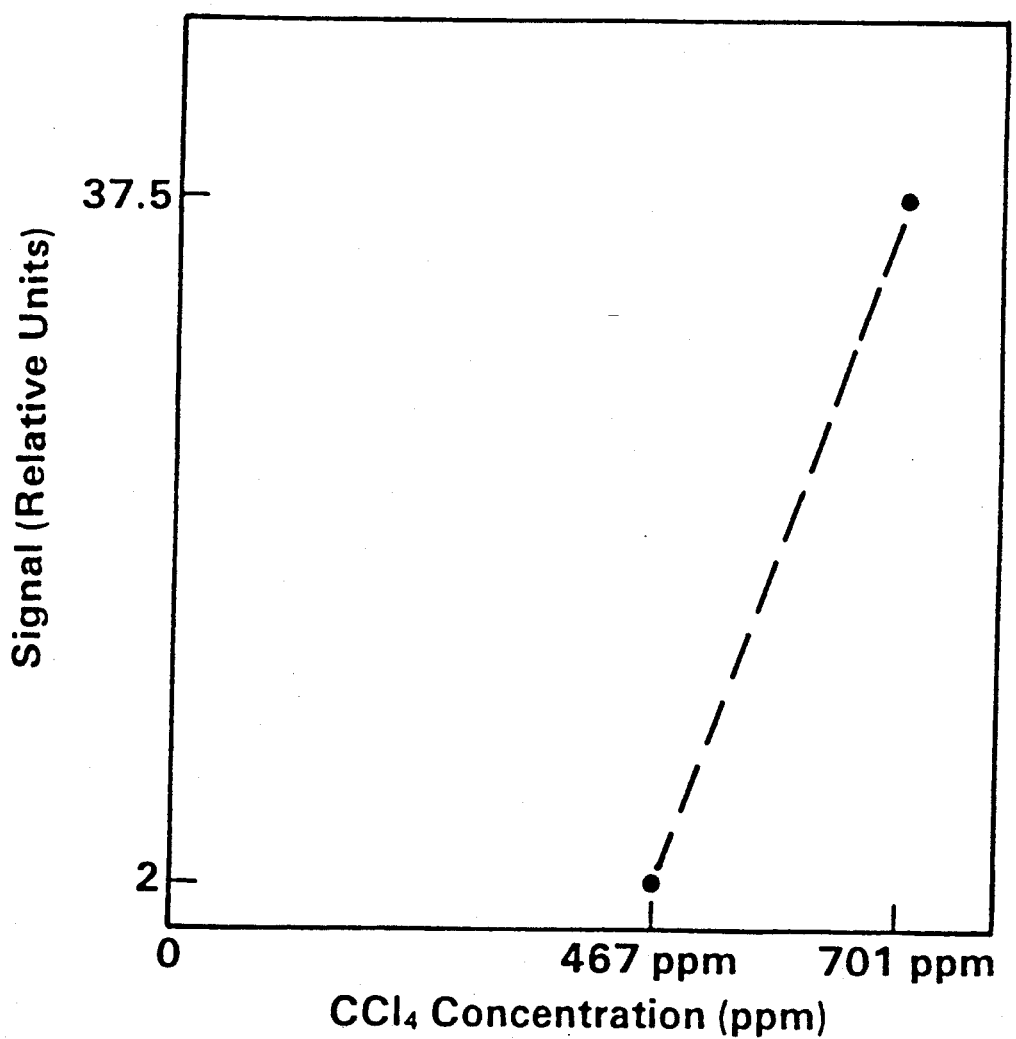
FIG. 13 shows the relative response of the helium plasma probe to carbon tetrachloride using the 837.6 nanometer emission line.

FIG. 13 shows the relative response of the helium plasma probe to carbon tetrachloride using the 837.6 nanometer emission line.

Spark Excitation

Figure 6:
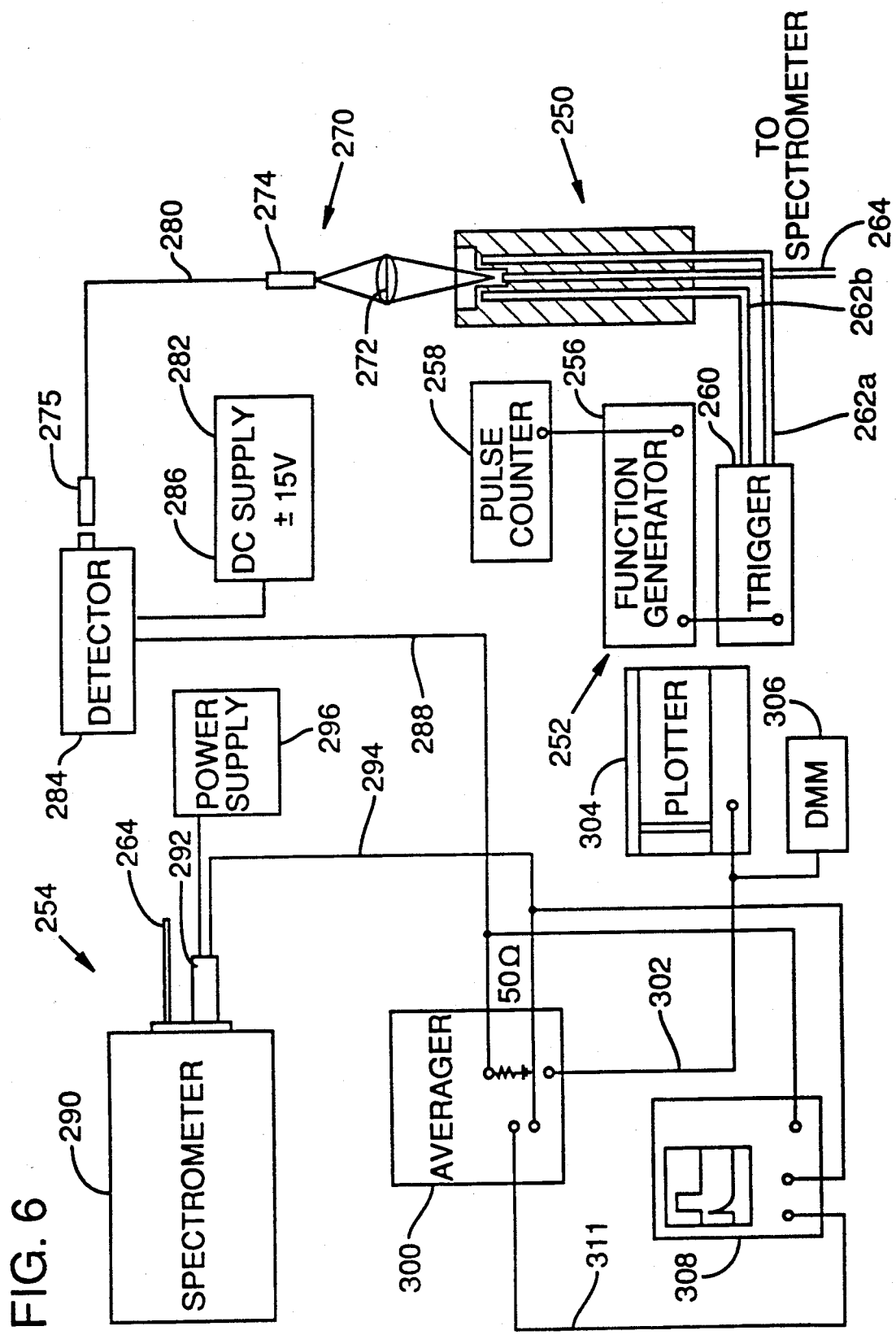
FIG. 6 is a schematic diagram of an example of a spark excitation apparatus, support equipment connected for operating the spark excitation apparatus and instrumentation connected for receiving, storing and analyzing data acquired from the spark excitation apparatus.

FIG. 6 is a schematic diagram showing the arrangement of a spark excitation probe 250, electrical signal generating equipment 252 for operating the spark probe 250, and instrumentation 254 for receiving and processing data acquired from the spark probe. The spark probe 250 is described in detail below with reference to FIG. 7.

The electrical signal generating equipment 252 includes a function generator 256, such as an HP model 3321A, connected to the trigger input of a trigger module 260, such as an EG&G model TM-11A. Trigger module 260 is capable of providing selected wave forms at voltages up to 30 Kv in response to trigger input signals. A pulse counter 258, such as a Data Precision model 5740, may be connected to function generator 256 to count the pulses provided by the function generator and thereby record the number of high voltage pulses output by trigger module 260. Trigger module 260 has two output conductors, each of which is connected to spark probe 250. The electrical signals are transmitted over conductors 262A and 262B, which are desirably high voltage cables.

The trigger detector apparatus 270 includes the following elements: A lens 272 is positioned to focus light emitted at the spark gap into a first end of a silica fiber optic cable 280. Fiber optic cable 280 is fitted with ferrules 274 and 275 at each end. The fiber optic cable 280 is axially aligned so that the spark gap lies along the fiber axis. A trigger detector 284 is positioned adjacent the ferrule 275 at the other end of fiber optic cable 280 to receive light emitted by the spark in spark probe 250. Detector 284 is powered by a power supply 286. Trigger detector 284 generates an electrical signal along path 288 that is responsive to light emission at the spark gap. This may be referred to as the trigger detector signal. Use of the trigger detector signal is described below.

Instrumentation 254 for processing data acquired from the spark probe is described next. Fiber optic cable 264 from spark probe 250 is terminated (butt mounted) at the entrance slit of a spectrometer 290, which is centered at 5000 Angstroms. The spectrometer 290 receives light transmitted through cable 264 at the entrance slit, and emits at the exit slit only light having a selected wavelength. Alternatively, the spectrometer may be operated to scan over a range of wavelengths at a predetermined scan rate. A photomultiplier apparatus 292 such as an Ortec model 269 photomultiplier base, is positioned adjacent the exit slit of spectrometer 290 so as to receive the emitted light. The photomultiplier 292 is powered by a power supply 296, such as an Ortec model 556 high voltage power supply. The photomultiplier generates an electrical signal along a path 294 responsive to light emitted through the exit slit.

A boxcar averager 300, such as an EG&G model PARC4121B, is connected to receive the trigger detector signal 288 at the trigger input and the electrical signal on path 294 at the signal input. The boxcar averager provides a data output signal on path 302. The data output signal can be recorded, for example, on a plotter 304, such as an HP model 7046A and/or measured on a digital multimeter 306 such as a Simpson model 461-2. An optional oscilloscope 308 is shown connected to display the boxcar averager gate output on a first trace and the photomultiplier output signal on a second trace.

In operation, function generator 256 is set to provide a periodic wave form to trigger the trigger module 260. The trigger module 260, accordingly, generates a periodic high voltage signal over path 262 to a pair of spark electrodes in spark probe 250. This results in a continuing series of sparks in the spark gap at a frequency, for example, of 20 pulses per second. Light from the spark is detected in the trigger detector 284 as described above and, in turn, it triggers the boxcar averager 300 to open the input gate at the time of each spark. Simultaneously, light from the region of the spark is provided over fiber optic cable 264 to the spectrometer 290. Light of selected wavelength stimulates the photomultiplier 292 to cause a responsive electrical signal 294 which is provided to the data input of the averager. Accordingly, the boxcar averager inputs data during each of a continuing series of time intervals, each interval beginning substantially contemporaneously with the initiation of a spark in spark probe 250. The gate output 311 of the box car averager 300 is coupled to a signal input of an oscilloscope 308 such as Tektronix model 7514. Data produced after the spark has subsided is ignored, as suggested by the display shown on the screen of oscilloscope 308. The parameters of an operative example of the foregoing apparatus is set forth in the following table:

TABLE III

Electro-Optical Detection System Parameters
Spark Probe

Box Car Averager

1. Gate Width: 6 micro seconds
2. Sensitivity: 100 mV, 1 V, 2 V
3. Input: DC/1 meg-ohm
4. Averaging: 10 pulse
5. Rep. Rate: 20 pps

Photomultiplier

1. Hamamatsu Tube #R1828.01 (WA1324) 84.11
2. Voltage: 1.2 KVDC

Spectrometer

Figure 7:
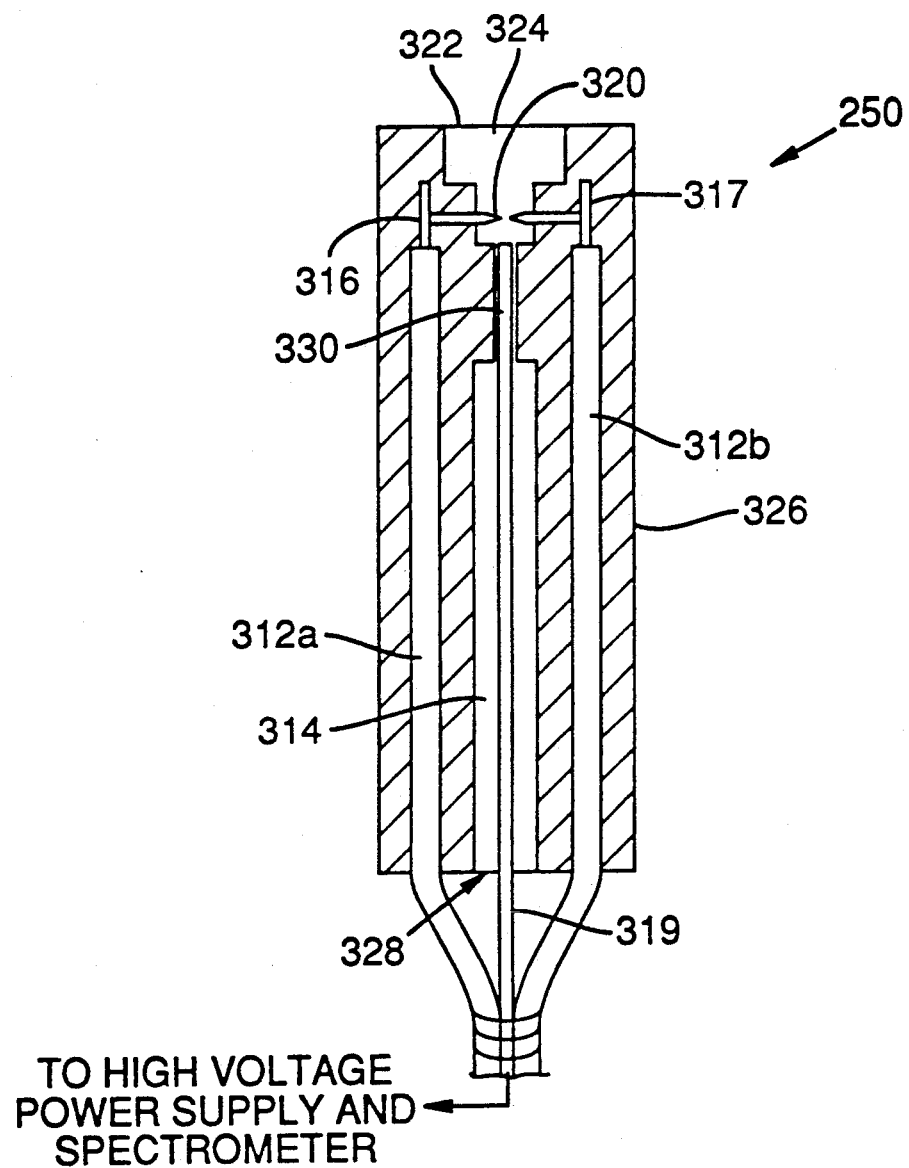
FIG. 7 is a cross-sectional side view of a spark probe suitable for use in the system of FIG. 1 in conjunction with support equipment and instrumentation such as shown in FIG. 6.

1. Slit: 200 microns
2. Filters: WG 335, GG475 (oriel)
3. Scan Rate: 1 angstrom/sec FIG. 7 shows additional detail of one embodiment of a spark probe suitable for use in the system of FIG. 6. Referring to FIG. 7, the spark, probe 250 includes a probe body 326 formed of a rigid, non-conductive material. Preferably, the probe body is formed of a polymeric material such as that sold under the brand name Delrin ® and is 1.25 inches in diameter by 6.5 inches in length. Probe body 326 is generally cylindrical, though its shape is not critical. Probe body 326 includes a central aperture 328 extending axially into the probe body from a first end. The central aperture 328 is sized for receiving an optical fiber 319 with a 1000 μm core encased in silicone cladding, and extends approximately two-thirds the length of the probe body. A terminal portion 330 of optical fiber 319 is shown in the end of the central aperture. The end of central aperture 328 is open to communicate with an analyte cavity 324. Analyte cavity 324 extends into the probe body 326 from the second end. The cavity may be covered by a screen or permeable membrane 322 for admitting analyte fluid into cavity 324.

Stranded conductors 312A and 312B extend into the first end of the probe body alongside the central aperture to positions adjacent the analyte cavity. A pair of thoriated tungsten electrodes 316, 317 are connected to conductors 312A, 312B respectively and positioned extending into cavity 324. Electrodes 316, 317 define a spark gap 320 axially aligned with fiber optic cable 319. The electrodes are 1/16" in diameter, 2% thoriated, and sharpened to a point such that the spark gap measures about 2 mm.

In one operative example of the spark probe, the optical fiber is formed of fused silica and has a 1,000 micron core. The probe body measures approximately 1.25" in diameter and is about 6.5" long. The stranded conductors 312A and 312B are made by Cable Silicones, Inc., AWM Style 3239, 25 kvdc.

Figure 8A:
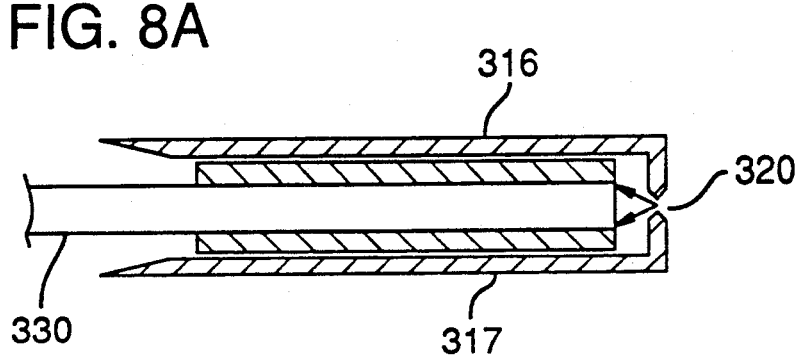
FIG. 8A is a schematic diagram of the analyte receiving end of a spark probe.
Figure 8B:
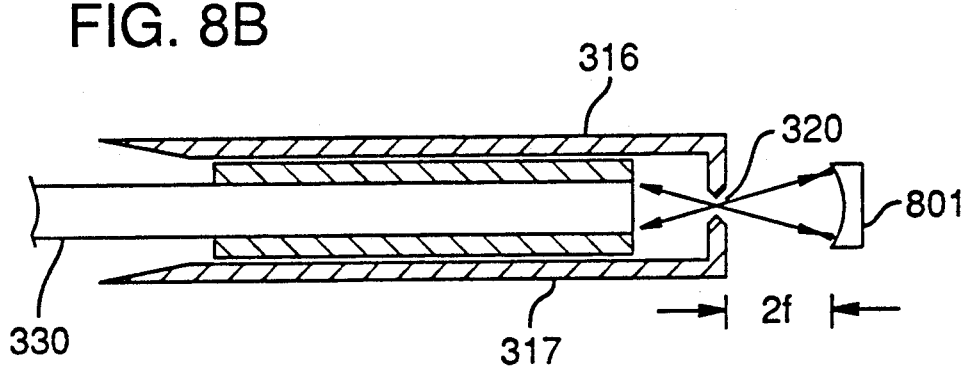
FIG. 8B is a schematic diagram of the analyte receiving end of a spark probe including a spherical mirror for collecting optical emissions from the area of the spark gap.
Figure 8C:
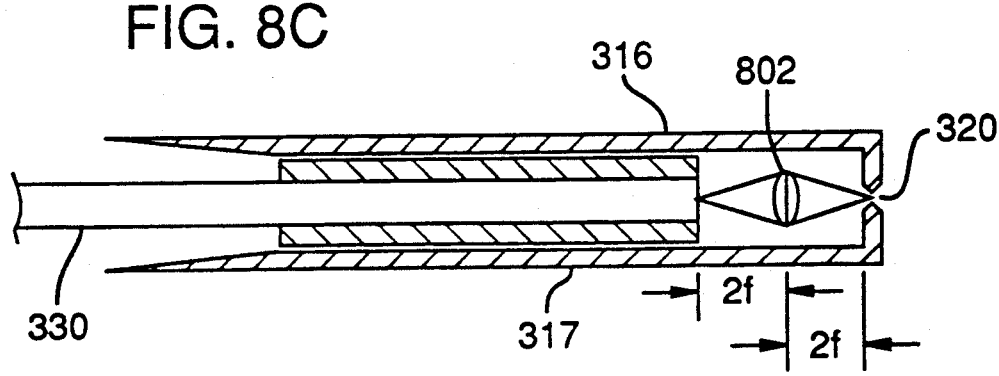
FIG. 8C is a schematic diagram of the analyte receiving end of a spark probe including a lens for collecting optical emissions from the area of the spark gap.

FIG. 8 shows three different arrangements for collecting emitted light at the spark gap end of the spark probe. FIG. 8A is an unfocused arrangement. FIG. 8B shows a spherical mirror 801 deployed for reflective collection of light. FIG. 8C shows a lens 802 employed for imaged collection of light from the region of the spark gap.

Figure 9:
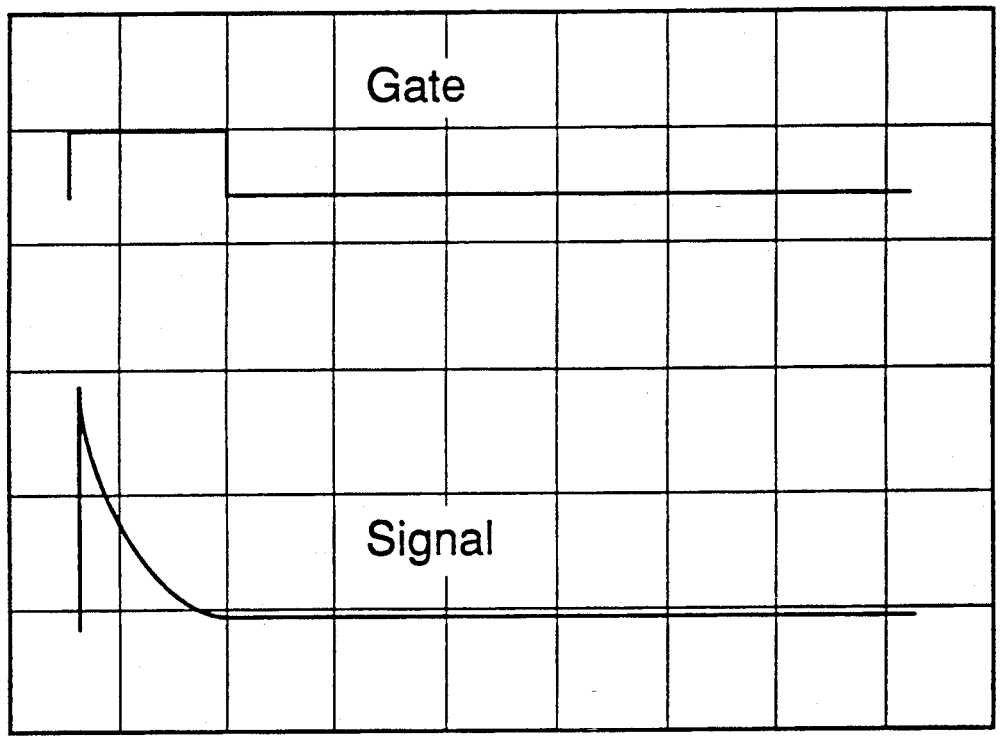
FIG. 9 shows an example of the boxcar averager gate and input signal waveforms produced by the system shown in FIG. 6.

FIG. 9 shows the boxcar averager gate and data input signal waveforms produced by the system shown in FIG. 6. In this display, the sweep rate is 5 microseconds per division, the sensitivity 200 Mv per division for the signal trace and 1 v per division for the gate trace.

Figure 10A:
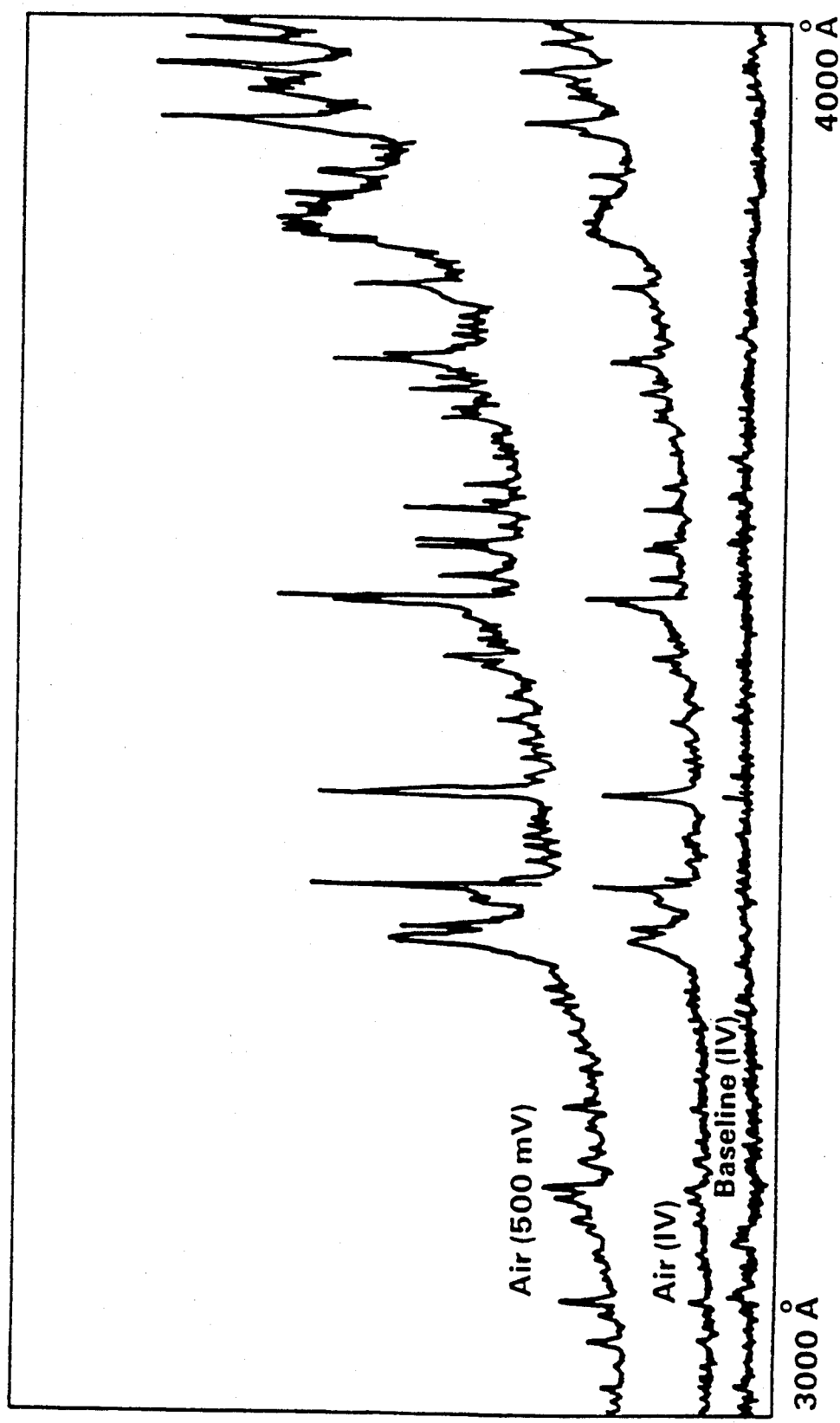
FIG. 10A covers wavelengths of 3,000 to 4,000 angstroms.
Figure 10B:
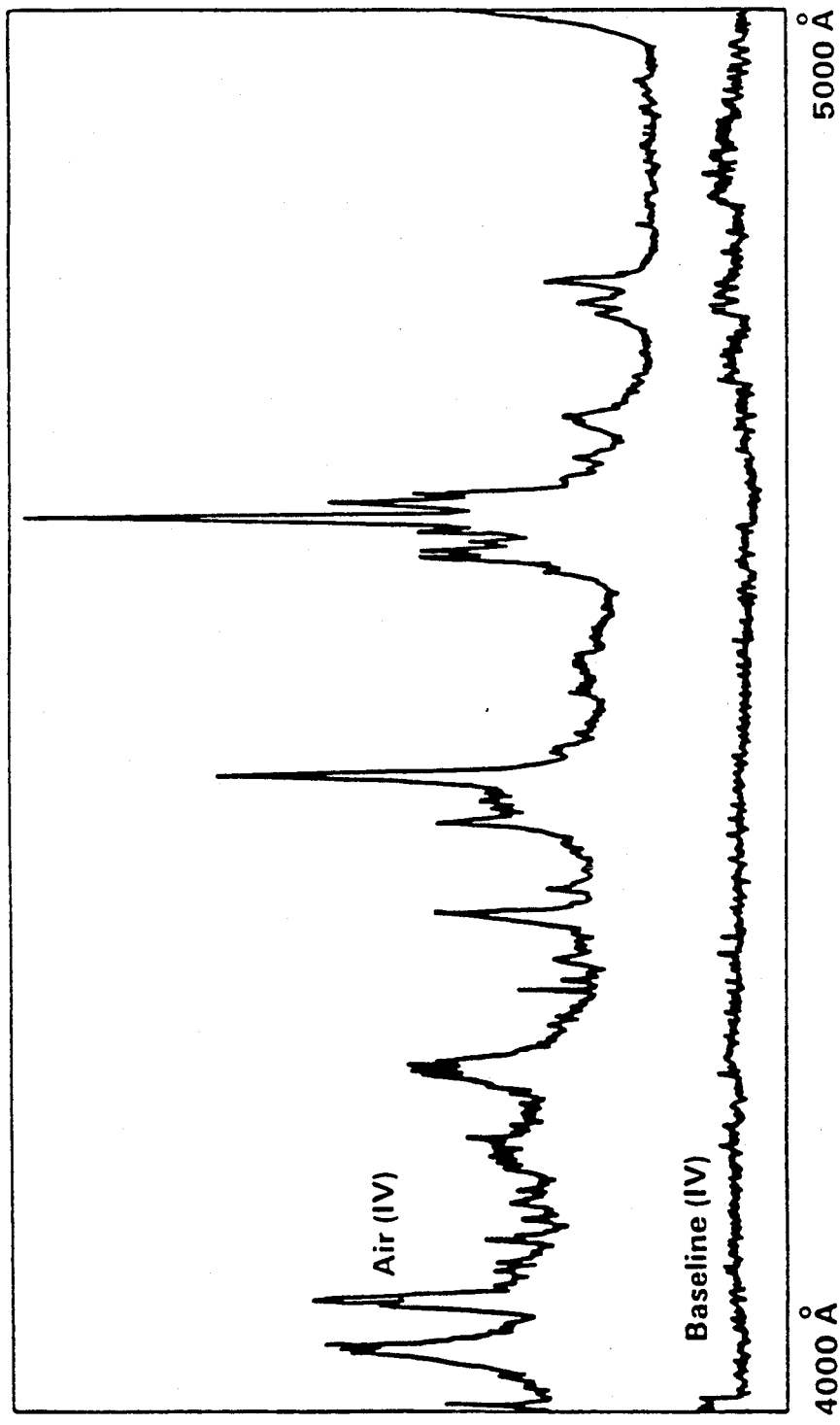
FIG. 10B covers wavelengths of 4,000 to 5,000 angstroms.
Figure 10C:
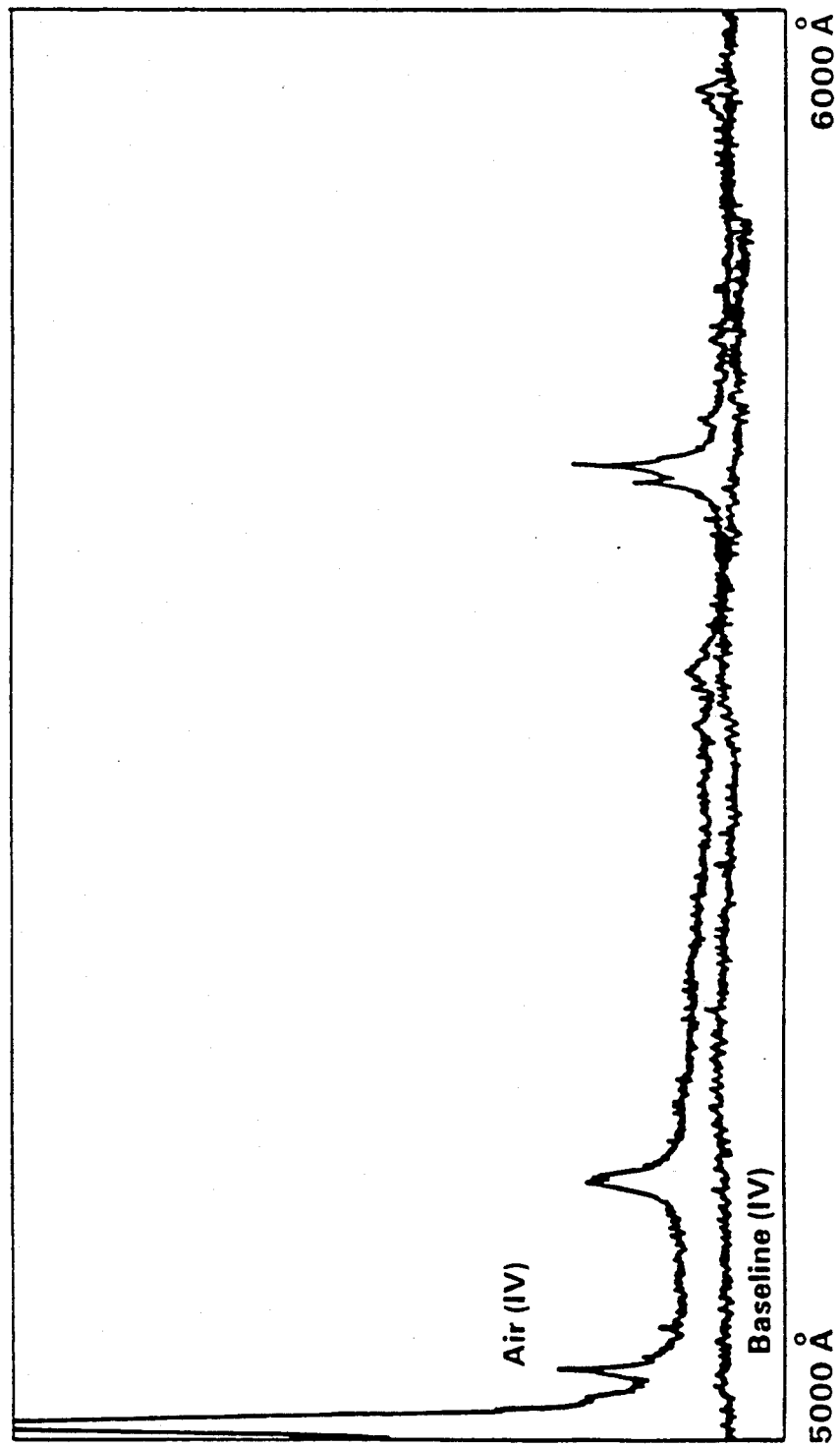
FIG. 10C covers wavelengths of 5,000 to 6,000 angstroms.

FIG. 10 is a spectral plot, or a spectrogram, generated by the spark probe apparatus for air, with a spark rate at 20 pps and the gate duration 6 microseconds. The spectral plot is presented in three parts: FIG. 10A covers wavelengths of 3,000 to 4,000 angstroms; FIG. 10B covers wavelengths of 4,000 to 4,000 angstroms; and FIG. 10C covers wavelengths of 5,000 to 6,000 angstroms. Operating parameters at the time the plot shown in FIG. 10 was made were as shown in the following table:

TABLE IV

Operating Parameters for the Spark Probe
Spectra For Air

Figure 11:
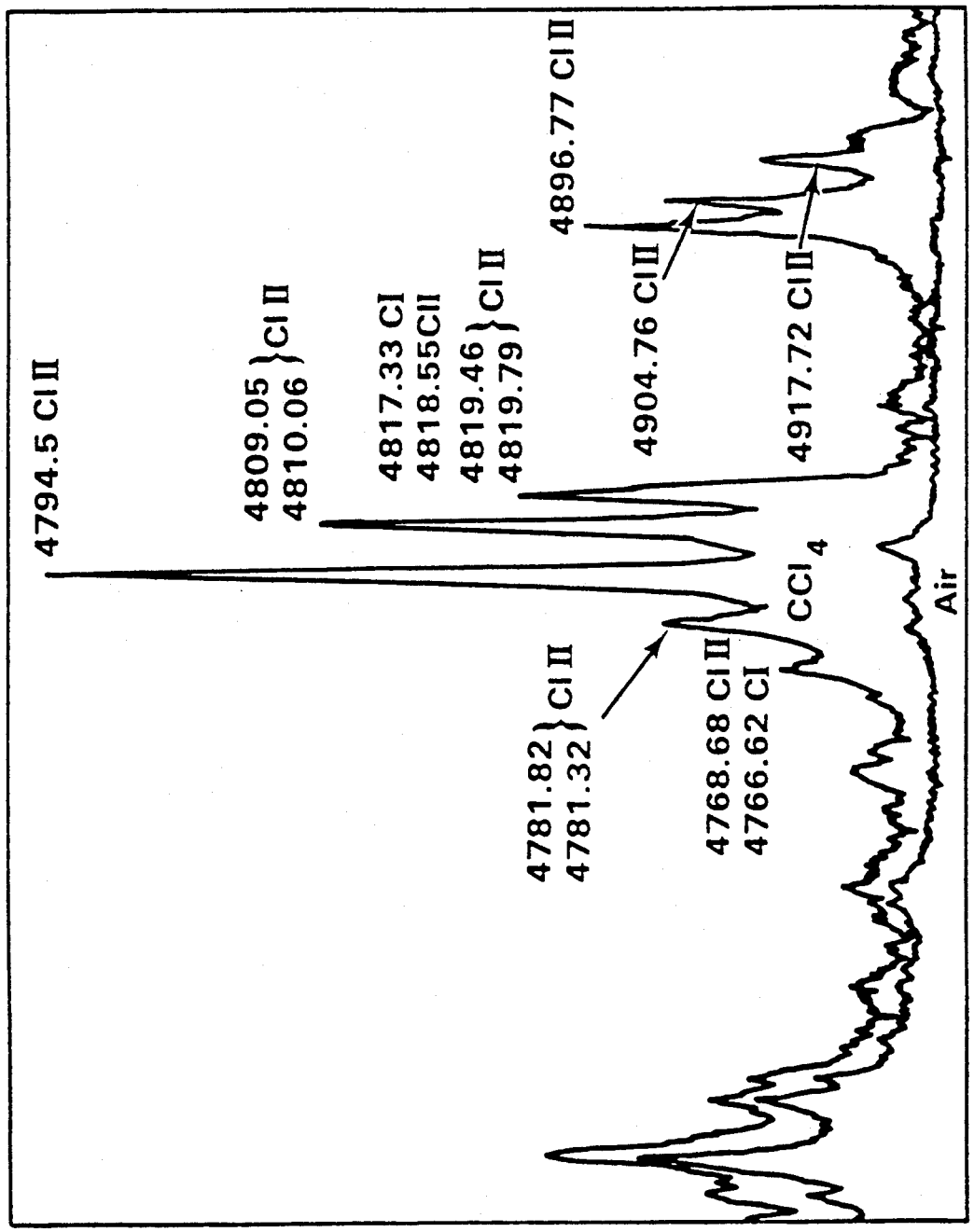
FIG. 11 is a spark probe spectral plot for air and $CCl_4$ (carbon tetrachloride).

PM Tube - 1.2 KV, 10 Sample Avg 1. 1.2 KV
2. 10 Sample Average
3. Plotter Settings: 1 V/inch, 100 seconds/inch FIG. 11 is a spark probe spectral plot for air and CCl4 (carbon tetrachloride). The spark rate is 20 Hz, 6 microsecond gate, no delay. The various spectral lines characteristic of carbon tetrachloride are identified in the figure.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

We claim:

1. A probe for analyzing of a fluid analyte for the presence of selected chemical species comprising:

an elongated probe body of a predetermined diameter having first and second ends;

an elongate light guide having first and second ends and defining an axis through said ends, a terminal portion of the light guide adjacent the first end extending axially into the first end of the probe body;

an electrical conductor having first and second ends connected at the first end to the probe for providing an electric signal to the probe;

means disposed in the second end of the probe body for admitting the fluid analyte axially of the first end of the light guide;

excitation means coupled to the first end of the conductor and responsive to the electric signal for exciting components of the fluid analyte along a portion of the light guide axis in proximity to the first end of the light guide;

the excitation means including an elongate capillary tube aligned about the light guide axis, the capillary tube having first and second ends and having input and discharge ports;

the first end of the capillary tube positioned in optical communication with the first end of the light guide;

the second end of the capillary tube connected to the analyte admitting means to receive analyte into the capillary tube;

a first tube connected to the input port for supplying inert gas;

a second tube connected to the discharge port for providing a vacuum source;

an electrode capacitively coupled to the capillary tube and connected to the conductor to receive the electric signal for exciting the inert gas; and a ground electrode coupled to the capillary tube for grounding current flow in the gas;

the light guide first end including means adapted to receive optical emissions from the excited components of the fluid analyte for transmitting the optical emissions to a detector coupled to the second end of the light guide.

2. A probe according to claim 1 wherein:

the electrode is a cylinder formed of stainless steel and it positioned concentrically about the capillary tube;

the capillary tube is formed of fused silica;

the light guide includes a fused silica fiber optic cable;

the probe further comprising a gradient index lens positioned between the first end of the capillary tube and the first end of the fiber optic cable for focusing optical emissions from the tube into the fiber optic cable.

3. A method of analyzing an ambient fluid analyte for the presence of selected chemical species comprising:

providing an elongate capillary tube defining a tube axis and having first and second ends and including an analyte port coupled to the first end to receive the fluid analyte, a gas inlet port adjacent the first end, coupled to a source of working gas suitable for maintaining a plasma, and a gas outlet port adjacent the second end;

applying a vacuum to the gas outlet port to draw the working gas and the ambient fluid analyte through the tube toward the gas outlet port; and applying RF electrical excitation to the tube intermediate the gas inlet and outlet ports to maintain a plasma in the tube for exciting components of the analyte.

4. A method according to claim 3 further comprising:

covering the second end of the tube with a window extending generally perpendicular to the tube axis and transparent to predetermined wavelengths of interest; and receiving spectral emissions within the predetermined wavelenths that are emitted through the window generally along the cell axis.

5. A method according to claim 4 wherein said receiving step includes:

providing a fiber optic cable having first and second ends;

positioning the first end of the fiber optic cable proximate the window so that at least a terminal portion of the cable adjacent the first end is aligned along the tube axis, for receiving the spectral emissions; and coupling the second end to a spectrometer for analysing the spectral emissions.

6. A system for in situ monitoring of a fluid analyte for the presence of selected chemical species, the system comprising:

a probe including:

an elongated probe body of a predetermined diameter having first and second ends;

an elongate light guide having first and second ends and defining an axis through said ends, a terminal portion of the light guide adjacent the first end extending axially into the first end of the probe body;

an electrical conductor having first and second ends connected at the first end to the probe for providing an electric signal to the probe; and means disposed in the second end of the probe body for admitting the fluid analyte axially of the first end of the light guide;

means in communication with the probe body for exhausting the fluid analyte so that, in use, fresh samples of fluid analyte can be continuously drawn through the probe body for continuously monitoring the analyte;

excitation means coupled to the first end of the conductor and responsive to the electric signal for exciting components of the fluid analyte along a portion of the light guide axis in proximity to the first end of the light guide;

the light guide first end including means adapted to receive optical emissions from the excited components of the fluid analyte for transmitting the optical emissions to the second end of the light guide;

an elongate cable having first and second ends and comprising the electrical conductor and the light guide, connected at the first end to the probe, for positioning the probe in contact with the fluid analyte;

power supply means connected to the second end of the conductor for providing the electrical signal to the excitation means; and detector means connected to the second end of the light guide for detecting the presence of selected wavelengths of light indicative of the presence of the selected chemical species.

7. A system according to claim 6 wherein:

the excitation means includes a plasma cell within the probe and a generally cylindrical electrode disposed about the plasma cell and coupled to the first end of the conductor so as to capacitively couple RF electrical signals from the conductor to the cell; and the cable further includes a first gas line coupled to the plasma cell for transmitting a working gas along the cable to supply the plasma cell, and a second gas line coupled to the plasma cell for withdrawing the working gas and the fluid analyte from the plasma cell to allow continuous operation.

8. A system according to claim 6 wherein the excitation means includes a pair of spaced apart electrodes defining a spark gap between the electrodes for generating a spark.

9. A system according to claim 8 including:

trigger means for generating a trigger signal responsive to the spark; and boxcar averager means responsive to the trigger signal and to the detection means for data collection.

10. A system according to claim 8 wherein the electrodes are formed of thoriated tungsten and the light guide is a fiber optical cable with the first end positioned adjacent the spark gap.

11. A system according to claim 10 wherein the probe body is formed of a substantially rigid, waterproof non-conductive material and includes:

means defining a first bore extending into the probe body from the first end alongside the fiber optical cable, size to receive a first wire;

means defining a second bore extending into the probe body from the first end alongside the fiber optic cable, sized to receive a second wire; and means defining an analyte cavity extending into the probe body from the second end to the first end of the fiber optic cable;

the conductor includes the first and second wires;

the analyte admitting means includes the analyte cavity; and the electrodes are positioned in the probe body so that one of the electrodes contacts the first wire and the other electrode contacts the second wire and each of the electrodes extends into the analyte cavity adjacent the first end of the fiber optic cable.

* * * * *

UNITED STATES PATENT AND TRADEMARK OFFICE
CERTIFICATE OF CORRECTION

PATENT NO. : 5,085,499
DATED : February 4, 1992
INVENTOR(S) : Griffin et al.

It is certified that error appears in the above-identified patent and that said Letters Patent is hereby corrected as shown below:

Column 1   Line 45, change "analysis" to --analysis.--;

Column 2   Line 5, change "metal" to --metal.--;

Column 2   Line 37, change "aerosols" to --aerosols.--;

Column 12  Line 43, change "7046A" to --7046A,--;

Column 14  Line 23, change "Avg" to --Avg.:--;

UNITED STATES PATENT AND TRADEMARK OFFICE
CERTIFICATE OF CORRECTION

PATENT NO. : 5,085,499
DATED : February 4, 1992
INVENTOR(S) : Griffin et al.

It is certified that error appears in the above-identified patent and that said Letters Patent is hereby corrected as shown below:

Column 16     Claim 10, Line 61, change "optical" to --optic--;

Column 16     Claim 11, Line 67, change "optical" to --optic--;

Column 16     Claim 11, Line 68, change "size" to --sized--.

Signed and Sealed this

First Day of February, 1994

BRUCE LEHMAN

*Attest:*

*Attesting Officer*     *Commissioner of Patents and Trademarks*